United States Patent [19]

Aunstrup

[11] 3,988,207
[45] Oct. 26, 1976

[54] PREPARATION OF A MILK-COAGULATING ENZYME

[75] Inventor: Knud Aunstrup, Hvidovre, Denmark

[73] Assignee: Novo Terapeutisk Laboratorium A/S, Copenhagen, Denmark

[22] Filed: Nov. 21, 1966

[21] Appl. No.: 595,643

[30] Foreign Application Priority Data

Dec. 2, 1965 United Kingdom.............. 51270/65

[52] U.S. Cl................................... 195/62; 195/65; 195/66 R
[51] Int. Cl.²........................................ C12D 13/10
[58] Field of Search............... 195/62, 66, 65, 66 R; 99/116

[56] References Cited
UNITED STATES PATENTS 3,212,905  10/1965  Arima et al.......................... 99/116

*Primary Examiner*—Lionel M. Shapiro
*Attorney, Agent, or Firm*—Fidelman, Wolffe & Waldron

EXEMPLARY CLAIM

1. A process for the preparation of a milk-coagulating enzyme which comprises cultivating a *Mucor miehei* Cooney et Emerson strain in a suitable nutrient medium, and then recovering the enzyme therefrom.

7 Claims, No Drawings

PREPARATION OF A MILK-COAGULATING ENZYME

The present invention relates to a process for the preparation of a milk-coagulating enzyme.

In the production of cheese it is necessary to coagulate the milk in order to be able to separate the casein from the whey. It is usual to employ an enzyme isolated from calf stomach in this process. In order to obtain a satisfactory yield of cheese and in view of the subsequent ripening of the cheese it is highly important that the proteolytic activity of the rennet enzyme is low, so that as little casein as possible dissolves during the production and ripening of the cheese.

Rennet from calf stomach is satisfactory for the above purpose. However, it is to be expected that the demand for rennet cannot be met with enzymes from calf stomach in the future. Thus, several attempts have been made in order to discover other milk-coagulating enzymes having low proteolytic activity.

A long series of micro-organisms produce proteinases having milk-coagulating effect, but most of these also possess a considerable proteolytic effect, so that the yield obtained in the production of cheese becomes too low, bitter tasting decomposition products of the casein (peptides) at the same time being formed during the cheese ripening. This applies to e.g. proteinases from *Bacillus subtilis* and *Aspergillus saitoi*.

Enzyme from *Mucor pusillus* appears to possess a more favourable ratio between milk-coagulating and proteolytic activity. However, this micro-organism would appear to be most suitable for surface cultivation and provides relatively low yields by submerged cultivation.

In accordance with the present invention it has now been found that it is possible to prepare a milk-coagulating enzyme in large yields and at a low cost by cultivating a *Mucor miehel* Cooney et Emerson strain or a natural or artificial variant or mutant thereof in a suitable nutrient medium.

The process of the invention is preferably carried out by means of submerged cultivation, but it is also possible to make use of surface cultivation in the present process.

In a preferred embodiment of the invention *Mucor miehei* Cooney et Emerson strain CBS 370.65 or a natural or artificial variant or mutant thereof is subjected to submerged cultivation in a suitable nutrient medium.

It is also within the scope of the invention to subject the latter strain CBS 370.65 or a natural or artificial variant or mutant thereof to surface cultivation in a suitable nutrient medium.

The new Mucor strain referred to above was isolated from compost collected in Copenhagen in September, 1965 and has been identified at Centraalbureau voor Schimmelculturen, Baarn, Holland as falling within the group *Mucor miehei* Cooney et Emerson. The new strain has been deposited at the above institution under the CBS number stated above.

In the following a morphological description of the above new Mucor CBS 370.65 is given:

Turf: Short, 2–3 mm high, at first white, later mouse-grey to dark mouse-grey;

Sporangiophores: 6–10 $\mu$ in diameter, branched sympodially;

Sporangia: Globose, 25–60 $\mu$ in diameter, walls beset with short spines;

Columellae: Subglobose to oval, 20–40 $\mu$ in diameter;

Sporangiospores: Colourless, subglobase to elliptical, 3–5 × 4–6 $\mu$.

Zygospores: Numerous, subglobose, warty, yellowish to reddish brown when young, blackish when mature, 30–45 $\mu$ in diameter, produced on a homothallic mycelium;

Azygospores present;

Gemmae unknown

Growth at 30°–55° C, very rapid at 40° C.

The preparation of a milk-coagulating enzyme by submerged cultivation in a nutrient medium of the above Mucor strain CBS 370.65 is illustrated in detail by way of example in the following:

1. Experiment using shake flasks.

A nutrient medium comprising

| | |
|---|---|
| Potato starch | 40 g per liter |
| Soy meal | 30 g per liter |
| Ground barley | 100 g per liter |
| CaCO$_3$ | 5 g per liter |
| Soya oil | 0.5 ml per liter | was employed.

Three 500 ml Erlenmeyer flasks each holding 100 ml of the above medium were inoculated with a spore suspension of *Mucor miehei* Cooney et Emerson CBS 370.65 and placed on a shaking table at 30° C for 7 days. The mycelium was filtered off, and the enzyme activity of the filtrate was determined by means of the Kunitz Method (J. Gen. Physiol. 18, 459 (1935)).

Flask I: 15800 Kunitz Rennet Units per liter

Flask II: 17700 Kunitz Rennet Units per liter

Flask III: 15700 Kunitz Rennet Units per liter.

2. Pilot plant experiment.

In an inoculation tank there was prepared a nutrient medium composed as follows:

| | |
|---|---|
| Potato starch | 2 kg |
| Soy meal | 1.5 kg |
| Barley flour | 5 kg |
| Bacterial Amylase Novo 5000 SKB | 5 g |
| CaCO$_3$ | 500 g |
| Water | about 40 liters |

The mixture was heated to about 70° C and kept at that temperature for about 30 minutes. The mixture was then boiled for 90 minutes at 120° C under direct injection of steam, the volume after cooling being about 50 liters. Following cooling to 34° C the medium was inoculated with spores from a Fernbach flask containing YPPSS-agar (Thermophilic Fungi Cooney & Emerson, London 1964) of the following composition:

| | |
|---|---|
| Yeast extract | 4 g |
| K$_2$HPO$_4$ | 1 g |
| MgSO$_4$. 7 H$_2$O | 0.5 g |
| Soluble starch | 15 g |
| Agar | 20 g |
| Water | 1000 ml |

The Fernbach flask had been inoculated with a lyophilized culture of *Mucor miehei* Cooney et Emerson CBS 370.65 and incubated at 40° C for sporulation.

After inoculation stirring (240 r.p.m.) and aeration

The composition of the medium has been stated in the table in grams per liter. In all of the media employed the starch was decomposed with bacterial amylase prior to sterilization.

Table

| Medium No. | 95 | 97 | 05 | 25 | 26 | 55 | 62 | 63 | 64 |
|---|---|---|---|---|---|---|---|---|---|
| Composition of medium in grams per liter | | | | | | | | | |
| Potato flour | 40 | 40 | | 40 | 40 | 40 | 40 | 40 | 40 |
| Soy meal | 30 | 30 | 30 | 30 | 30 | 30 | 20 | 20 | 20 |
| Ground barley | 100 | | 100 | 100 | 50 | 100 | 100 | 100 | 100 |
| Ground corn | | 100 | | | 50 | | | | |
| Ground corn germ | | | | | | | 10 | | |
| Yellow pea flour | | | | | | | | 10 | |
| Rice flour | | | 40 | | | | | | |
| Soludry | | | | | | | | | 10 |
| $Na_2SO_4$ | 1 | 1 | 1 | 1 | 1 | 1 | 1 | 1 | 1 |
| $CaCO_3$ | 5 | 5 | 5 | 5 | 5 | 5 | 5 | 5 | 5 |
| $KH_2PO_4$ | 3 | 3 | 3 | 3 | 3 | 3 | 3 | 3 | 3 |
| Enzyme activity KRU/ml after incubation in 6 days | 13,5 | 9,7 | 11,5 | 13,6 | 13,6 | 12,0 | 2,6 | 7,1 | 4,9 |
| 7 days | 15,4 | 10,7 | 11,9 | 19,2 | 17,8 | 13,2 | 13,3 | 14,8 | 14,0 |
| 8 days | 17,2 | 14,6 | 13,8 | 21,2 | 18,2 | 14,6 | 12,9 | 16,7 | 15,4 |
| pH after incubation in 6 days | 6,1 | 6,1 | 7,0 | 6,1 | 6,0 | 6,2 | 6,1 | 6,2 | 5,9 |
| 7 days | 6,9 | 7,1 | 6,8 | 6,5 | 6,7 | 6,8 | 6,0 | 6,4 | 6,3 |
| 8 days | 7,0 | 7,2 | 7,5 | 6,9 | 6,8 | 6,9 | 6,7 | 6,2 | 6,3 |

(60 liters per minute) were started. Fermentation was continued for 48 hours until a good growth in the tank was observed.

The contents of the tank were then transferred to a main fermentation tank containing:

| | |
|---|---|
| Potato starch | 8 kg |
| Soy meal | 6 kg |
| Ground barley | 20 kg |
| Bacterial Amylase Novo 5000 SKB | 25 g |
| $CaCO_3$ | 2 kg |

The medium was boiled and sterilized in the same manner as the inoculation tank medium, and the final volume was 200 liters.

After the inoculation stirring was started (400 r.p.m.) as well as aeration (0.2 m³ per minute), and soya oil was added as an anti-foaming agent when necessary. During fermentation the pH-value was constant at 6.5.

After 129 hours the milk-coagulating enzyme content of the culture liquid was 2580 Kunitz Rennet Units per liter.

3. Additional shake flask experiment.

500 ml Erlenmeyer flasks each holding 100 ml of the medium (vide the following table) were used. The flasks were incubated at 30° C on a rotating shaking table (240 r.p.m. for the periods of time stated in the following table.

The inoculating material was a spora suspension prepared by cultivating *Mucor miehei* Cooney et Emerson CBS 370.65 on YPPSS-agar at 40° C for 2–3 days and washing the spores off with sterile water. YPPSS-agar has the composition stated in the foregoing.

The milk-coagulating enzyme activity was determined in accordance with Kunitz and was expressed in KRU (Kunitz Rennet Units).

Yields of milk-coagulating enzyme of the same order as obtained in the above shake flask experiments may also be attained when operating in pilot plants on a larger scale.

4. As a further illustration, milk-coagulating enzyme produced in a corresponding manner using *Mucor pusillus* (provided by Centraalbureau voor Schimmelculturen, Baarn, Holland) was obtained in an amount of about 300 Kunitz Rennet Units per liter (Medium 95, vide above; shake flask), whereas milk-coagulating enzyme produced by means of *Mucor miehei* CBS 370.65 was obtained in an amount of about 10,000 Kunitz Rennet Units per liter or even considerably more.

When a medium consisting of 10% skimmed milk, 1% glucose, 0.1% yeast extract and 0.005 M $CaCl_2$ was employed, the following results were obtained.

Mucor pusillus: 900 Kunits Rennet Units per liter
Mucor miehei CBS 370.65:5500 Kunitz Rennet Units per liter 5. Example of surface cultivation.

In 500 ml Erlenmeyer flasks 25 g of a mixture of wheat bran and water (1:1) was sterilized. The flasks were sterilized by heating to 120° C for 45 minutes, and after cooling to 40° C they were inoculated with spores of *Mucor miehei* Cooney et Emerson strain CBS 370.65 as described above. The flasks were incubated for 3 days at 40° C. The bran was then extracted with 200 ml of water, and the milk-coagulating activity of the extract was found to be 4500 KRU per liter.

The milk-coagulating enzyme prepared in accordance with the method of the invention is compared with rennet from calf stomach in the following:

The activity against sodium caseinate at pH 6.3 and 37° C is compared with that of rennin. The same amount of KRU of the two enzymes were used, and the optical density (OD) was determined at 280 mμ after precipitation with trichloroacetic acid. After 180 minutes the OD for the rennin-treated caseinate had not altered (constant at 0.137) while the OD for *Mucor miehei* enzyme had increased from 0.136 to 0.265, an increase which is rather insignificant in practical cheese making.

The milk-coagulating enzyme prepared according to the method of the present invention has been employed in the production of cheese, and satisfactory taste and yields have been obtained.

What I claim is:

1. A process for the preparation of a milk-coagulating enzyme which comprises cultivating a *Mucor miehei* Cooney et Emerson strain in a suitable nutrient medium, and then recovering the enzyme thereform.

2. A process as claimed in claim 1, which comprises cultivating a *Mucor miehei* Cooney et Emerson strain by submerged cultivation in a suitable nutrient medium.

3. A process as claimed in claim 1, which comprises cultivating a *Mucor miehei* Cooney et Emerson strain by surface cultivation in a suitable nutrient medium.

4. A process as claimed in claim 2, which comprises cultivating *Mucor miehei* Cooney et Emerson Strain CBS 370.65 by submerged cultivation in a suitable nutrient medium.

5. A process as claimed in claim 3, which comprises cultivating *Mucor miehei* Cooney et Emerson Strain CBS 370.65 by surface cultivation in a suitable nutrient medium.

6. A milk-coagulating enzyme prepared by the process of claim 1.

7. A process for the preparation of a milk-coagulating enzyme which comprises cultivating a milk-coagulating enzyme producing strain of *Mucor miehei* Cooney et Emerson in a suitable nutrient medium, and thereafter recovering the milk-coagulating enzyme from the medium.

* * * * *

UNITED STATES PATENT OFFICE
CERTIFICATE OF CORRECTION

PATENT NO. : 3,988,207
DATED : November 21, 1966
INVENTOR(S) : Knud Aunstrup

It is certified that error appears in the above-identified patent and that said Letters Patent are hereby corrected as shown below:

Columns 3-4 of the above patent delete the table as shown and add the following corrected table:

Table

| Medium No. | | 95 | 97 | 05 | 25 | 26 | 55 | 62 | 63 | 64 |
|---|---|---|---|---|---|---|---|---|---|---|
| Composition of medium in grams per liter | | | | | | | | | | |
| Potato flour | | 40 | 40 | | 40 | 40 | 40 | 40 | 40 | 40 |
| Soy meal | | 30 | 30 | 30 | 30 | 30 | 30 | 20 | 20 | 20 |
| Ground barley | | 100 | | 100 | 100 | 50 | 100 | 100 | 100 | 100 |
| Ground corn | | | 100 | | | 50 | | | | |
| Ground corn germ | | | | | | | | 10 | | |
| Yellow pea flour | | | | | | | | | 10 | |
| Rice flour | | | | 40 | | | | | | 10 |
| Soludry | | | | | | | | | .1 | |
| $Na_2SO_4$ | | 1 | 1 | 1 | 1 | 1 | 1 | 1 | 1 | 1 |
| $CaCO_3$ | | 5 | 5 | 5 | 5 | 5 | 5 | 5 | 5 | 5 |
| $KH_2PO_4$ | | 3 | 3 | 3 | 3 | 3 | 3 | 3 | 3 | 3 |
| Enzyme activity KRU/ml after incubation in | 6 days | 13.5 | 9.7 | 11.5 | 13.6 | 13.6 | 12.0 | 2.6 | 7.1 | 4.9 |
| | 7 days | 15.4 | 10.7 | 11.9 | 19.2 | 17.8 | 13.2 | 13.3 | 14.8 | 14.0 |
| | 8 days | 17.2 | 14.6 | 13.8 | 21.2 | 18.2 | 14.6 | 12.9 | 16.7 | 15.4 |
| pH after incubation in | 6 days | 6.1 | 6.1 | 7.0 | 6.1 | 6.0 | 6.2 | 6.1 | 6.2 | 5.9 |
| | 7 days | 6.9 | 7.1 | 6.8 | 6.5 | 6.7 | 6.8 | 6.0 | 6.4 | 6.3 |
| | 8 days | 7.0 | 7.2 | 7.5 | 6.9 | 6.8 | 6.9 | 6.7 | 6.2 | 6.3 |

Signed and Sealed this

First Day of February 1977

[SEAL]

Attest:

RUTH C. MASON
Attesting Officer

C. MARSHALL DANN
Commissioner of Patents and Trademarks